United States Patent [19]

Alfano et al.

[11] Patent Number: 5,939,048

[45] Date of Patent: *Aug. 17, 1999

[54] TASTE MASKED DESENSITIZING COMPOSITIONS

[75] Inventors: Michael C. Alfano, Franklin Lake; Joseph D. Synodis, Summitt; Alfred J. Smetana, Wayne; Ronald S. Leight, Aderdeen; Kuo-Chen Yeh, Westfield, all of N.J.

[73] Assignee: Block Drug Co., Inc., Jersey City, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/674,797

[22] Filed: Jul. 3, 1996

Related U.S. Application Data

[63] Continuation of application No. 08/309,134, Sep. 20, 1994, abandoned.

[51] Int. Cl.$^6$ .............................. A61K 7/16; A61K 33/10
[52] U.S. Cl. ............................ 424/49; 424/717
[58] Field of Search .................. 424/49–58, 717

[56] References Cited

U.S. PATENT DOCUMENTS

| | | | |
|---|---|---|---|
| 3,772,431 | 11/1973 | Mlkvy et al. | 424/44 |
| 3,821,368 | 6/1974 | Reynolds | 424/128 |
| 3,875,311 | 4/1975 | Eisenstadt | 426/212 |
| 3,875,312 | 4/1975 | Eisenstadt | 426/212 |
| 3,886,266 | 5/1975 | Goloman et al. | 424/53 |
| 3,888,976 | 6/1975 | Mlkvy et al. | 424/44 |
| 3,932,608 | 1/1976 | Anderson et al. | 424/54 |
| 3,935,304 | 1/1976 | Januszewski et al. | 424/49 |
| 3,935,305 | 1/1976 | Delaney et al. | 424/49 |
| 3,937,321 | 2/1976 | Delaney et al. | 206/84 |
| 3,937,803 | 2/1976 | Delaney et al. | 424/49 |
| 3,937,804 | 2/1976 | Delaney et al. | 424/52 |
| 3,943,240 | 3/1976 | Delaney et al. | 424/49 |
| 4,024,237 | 5/1977 | Eichel et al. | 424/49 |
| 4,302,441 | 11/1981 | Muhlemann et al. | 424/48 |
| 4,348,378 | 9/1982 | Kosti | 424/7 |
| 4,367,218 | 1/1983 | Jacobson | 424/49 |
| 4,416,867 | 11/1983 | Ritchey et al. | 424/49 |
| 4,436,720 | 3/1984 | Pakhomov et al. | 424/44 |
| 4,487,757 | 12/1984 | Kiozpeoplou | 424/7.1 |
| 4,514,094 | 4/1985 | Buckholz et al. | 366/160 |
| 4,521,403 | 6/1985 | Simon et al. | 424/31 |
| 4,522,805 | 6/1985 | Gordon | 424/52 |
| 4,547,362 | 10/1985 | Winston et al. | 424/49 |
| 4,575,375 | 3/1986 | Kozam | 604/185 |
| 4,575,457 | 3/1986 | Mazarin | 424/52 |
| 4,592,488 | 6/1986 | Simon et al. | 222/94 |
| 4,592,489 | 6/1986 | Simon et al. | 222/94 |
| 4,603,045 | 7/1986 | Smigel | 424/52 |
| 4,606,912 | 8/1986 | Rudy et al. | 424/52 |
| 4,610,873 | 9/1986 | Rudy et al. | 424/52 |
| 4,623,536 | 11/1986 | Winston et al. | 424/49 |
| 4,631,185 | 12/1986 | Kim | 424/49 |
| 4,639,368 | 1/1987 | Niazi et al. | 424/48 |
| 4,663,153 | 5/1987 | Winston et al. | 424/52 |
| 4,665,902 | 5/1987 | Spector | 128/62 |
| 4,690,772 | 9/1987 | Tell et al. | 252/106 |
| 4,690,776 | 9/1987 | Smigel | 252/315.3 |
| 4,721,614 | 1/1988 | Winston et al. | 424/52 |
| 4,751,072 | 6/1988 | Kim | 424/49 |
| 4,776,500 | 10/1988 | Ford | 222/402.1 |
| 4,812,306 | 3/1989 | Cocherell et al. | 424/52 |
| 4,812,308 | 3/1989 | Winston et al. | 424/52 |
| 4,814,163 | 3/1989 | Barth | 424/49 |
| 4,837,008 | 6/1989 | Rudy et al. | 424/53 |
| 4,839,158 | 6/1989 | Michaels | 424/54 |
| 4,891,201 | 1/1990 | Winston | 424/52 |
| 4,897,258 | 1/1990 | Rudy et al. | 424/53 |
| 4,925,655 | 5/1990 | Smigel et al. | 424/52 |
| 4,943,429 | 7/1990 | Winston et al. | 424/52 |
| 4,971,782 | 11/1990 | Rudy et al. | 424/53 |
| 4,976,955 | 12/1990 | Libin | 424/53 |
| 5,000,942 | 3/1991 | Libin | 424/53 |
| 5,004,596 | 4/1991 | Cocherell et al. | 424/52 |
| 5,098,711 | 3/1992 | Hill et al. | 424/401 |
| 5,124,144 | 6/1992 | Giorgetti et al. | 424/78.01 |
| 5,165,913 | 11/1992 | Hill et al. | 424/49 |
| 5,180,576 | 1/1993 | Winston et al. | 424/52 |
| 5,182,099 | 1/1993 | Jonsson et al. | 424/49 |
| 5,188,822 | 2/1993 | Viccaro et al. | 424/52 |
| 5,240,697 | 8/1993 | Norfleet et al. | 424/52 |
| 5,294,432 | 3/1994 | Winston et al. | 424/52 |
| 5,302,373 | 4/1994 | Giacin et al. | 424/49 |
| 5,318,773 | 6/1994 | Winston et al. | 424/52 |
| 5,330,749 | 7/1994 | Giacin et al. | 424/49 |
| 5,352,439 | 10/1994 | Norfleet et al. | 424/52 |
| 5,374,417 | 12/1994 | Norfleet et al. | 424/74 |
| 5,376,360 | 12/1994 | Dumkks et al. | 424/52 |
| 5,385,727 | 1/1995 | Winston et al. | 424/49 |
| 5,422,087 | 6/1995 | Lajoie | 423/267 |
| 5,424,074 | 6/1995 | Koli et al. | 424/464 |
| 5,455,023 | 10/1995 | Giacin et al. | 424/49 |

FOREIGN PATENT DOCUMENTS 9534274  12/1995  WIPO .

*Primary Examiner*—Shep K. Rose
*Attorney, Agent, or Firm*—Ostrolenk, Faber, Gerb & Soffen, LLP

[57] ABSTRACT

An oral composition for treatment of hypersensitive teeth in which the salty taste of the desensitizing salt, such as a potassium or strontium salt, is masked by baking soda, sodium bicarbonate.

18 Claims, No Drawings

5,939,048

TASTE MASKED DESENSITIZING COMPOSITIONS

This is a continuation of application Ser. No. 08/309,134, filed Sep. 20, 1994, abandoned.

FIELD OF THE INVENTION

The invention is directed to methods and compositions for desensitizing hypersensitive teeth.

DESCRIPTION OF RELATED ART

The sensory nerves of the teeth are subject to stimuli from various sources, including heat, cold, sugars, hypertonic solutions and the like. Usually, these various stimuli do not disturb the normal functioning of the dental sensory nerves. However, when the sensory nerves become more easily excitable for example, because of dental erosion, gum recession, exposure of the dentin or other causes, the teeth are more sensitive than usual to stimuli, resulting in distress and pain. When such an elevation of sensory nerve activity occurs, it is necessary to reduce the dental sensory nerve activity and to desensitize the hypersensitive dentin in order to reduce or relieve the pain. One way of accomplishing this result is to apply to the dentin an effective amount of a substance which can reduce sensory nerve activity and desensitize the hypersensitive dentin.

Potassium and strontium salts have long been recognized as desensitizing agents. Potassium chloride (U.S. Pat. No. 4,751,072 to Kim, issued Jun. 14, 1988), potassium bicarbonate (U.S. Pat. No. 4,631,185 to Kim), potassium nitrate (U.S. Pat. No. 3,863,006 to Hodosh, issued Jan. 28, 1975) and strontium chloride (U.S. Pat. No. 3,122,483 to Rosenthal, issued Feb. 25, 1964) have all been recognized as effective desensitizers. These ingredients may be incorporated into oral care compositions, including dentifrices, chewing gums and liquid solutions for application in a dentist's office.

Desensitizing compositions containing strontium, potassium or other salts, not surprisingly, can have strong salty tastes. Unfortunately, this salty taste, including a strong salty aftertaste, can reduce consumer compliance with desensitizing regimens and usage of desensitizing compositions.

Despite great strides in improving the flavor, hedonics and organoleptic qualities of these compositions by using mint flavors and gel formulations, desensitizing dentifrices still have both a salty taste and a salty aftertaste. The salty taste and aftertaste may prevent or discourage persons with dental hypersensitivity from using a desensitizing oral composition, resulting in reduced usage of the oral composition and resulting unnecessary discomfort for such persons.

Taste masking per se is not new. It has long been known that, as a general proposition, one type of taste, such as the sweet taste of sugar or sugar substitutes may successfully mask a different type of taste such as the bitter, sour or salty taste of many medicaments.

Surprisingly, it has now been discovered that one salt, sodium bicarbonate, can successfully mask the salty flavor of other, desensitizing, salts when the salts are combined in oral care compositions.

Sodium bicarbonate, commonly known as baking soda, has been used for many years in toothpastes as an abrasive. Baking soda has also enjoyed some popularity as an ingredient in general purpose toothpastes and other oral care products such as dental floss and tooth powder. While these oral care products provide adequate dental care, they do not provide a desensitizing active ingredient for those suffering from dental hypersensitivity.

Although sodium bicarbonate has been used as an abrasive in dentifrices, it has not been without drawbacks. In U.S. Pat. No. 4,547,362 to Winston et al., issued Oct. 15, 1985, for example, states, "another major problem encountered in formulating a tooth powder containing sodium bicarbonate particles is the salty taste of sodium bicarbonate." That patent proposed using coarse grades of sodium bicarbonate and flavoring and sweetening agents to help "mask the salty taste of the sodium bicarbonate."

Even in anhydrous toothpastes, sodium bicarbonate has drawbacks. In U.S. Pat. No. 5,004,596 to Cocherell et al., issued Apr. 2, 1991, an anhydrous toothpastes or dental creme may contain an inorganic salt selected from sodium bicarbonate, magnesium sulfate and sodium chloride. The patent states, "No single flavoring oil will mask the taste of the sodium bicarbonate and/or other salts used in this formula."

Several commercial brands of toothpaste use baking soda, but we are not aware of any commercial dentifrice that has both a desensitizing salt and baking soda.

The astounding result that one salt may successfully mask the salty taste of another salt is entirely unexpected and not suggested by any source known to the inventors hereof. But, one patent does list the combination of potassium nitrate and sodium bicarbonate as a theoretical possibility. U.S. Pat. No. 5,182,099 to Jonsson, issued Jan. 26, 1993 is directed to a preparation for prevention of emission of mercury from amalgam fillings. The composition comprises sulfur and may be a toothpaste. In addition to sulfur, the patent lists 62 permissible ingredients for the toothpaste, including sodium bicarbonate (ingredient no. 40) and potassium nitrate (ingredient no. 30).

Sodium bicarbonate has been used as part of a taste masking system for generating a carbon dioxide anaesthetic in U.S. Pat. No. 4,639,368 to Niazi et al., issued Jan. 27, 1987. That patent is directed to chewing gums containing a medicament and a taste masking agent. The medicament may be a broad range of compounds. As stated in the patent, "Many of the medicaments useful in the present invention have an unpleasant taste . . . . Natural and/or artificial sweeteners may be used, but are not entirely satisfactory because the taste of the medicament is often so strong that it overpowers the sweetener. However, the taste of the medicament may be effectively masked by the use of compounds or mixtures capable of generating carbon dioxide."

The preferred carbon dioxide generator of the '368 patent produces a local topical anaesthetic effect. The carbon dioxide can be provided "via an effervescent reaction between, for example, a water soluble bicarbonate salt, such as sodium bicarbonate, and an organic acid suitable for human consumption, such as tartaric acid . . . . " Additional anesthetics may be used if the carbon dioxide is insufficient to mask the medicament fully.

Sodium bicarbonate has also been used to modify the flavor profile of aspartame in U.S. Pat. No. 3,875,311 and U.S. Pat. No. 3,875,312, both to Eisenstadt, issued Apr. 1, 1975.

One floss patent, U.S. Pat. No. 5,165,913 to Hill et al., issued Nov. 24, 1992, uses, inter alia, sodium bicarbonate as a solid, insoluble particle to control viscosity of a melt-emulsion used to treat the floss during manufacturing, to modify the solid texture of the completed product, to impart beneficial and pleasant mouth feel properties to the product which are perceived during use, and to optimize cleaning. Sodium bicarbonate is also used as a buffer. one set of examples in the patent uses strontium chloride and potassium nitrate as desensitizers in the floss, but whether sodium bicarbonate is also used is unclear.

Breslin and Beauchamp in the Fifteenth Annual Meeting of the Association for Chemoreception Sciences (reported in *Chemical Senses*, vol. 18, no. 5, pp. 523–659, paragraph 25 (1993)) report that bitterness of certain compounds can be reduced in some instances by addition of salty compounds such as NaCl, but that the tested bitter compounds did not suppress the saltiness of the NaCl. Potassium chloride, KCl, however, did not suppress the bitter flavor of urea. It thus appears that taste-masking remains a highly unpredictable art.

A strong need remains in the art for a desensitizing oral composition with a dramatically improved flavor profile. The invention answers that strong need.

SUMMARY OF THE INVENTION

The principal object of the invention therefore is to provide a pleasant-tasting oral composition useful for treatment of hypersensitive teeth.

An additional object of the invention is to provide a method for treating hypersensitive teeth with a pleasant-tasting composition for relieving pain and discomfort related to dental hypersensitivity.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides an oral composition comprising a desensitizing salt and sodium bicarbonate.

To further achieve the foregoing objects and in accordance with the purpose of the invention, the invention further provides a method for treating dental hypersensitivity by administering to a hypersensitive tooth a composition comprising a desensitizing salt and sodium bicarbonate.

DESCRIPTION OF THE PREFERRED EMBODIMENTS

While this specification concludes with claims particularly pointing out and distinctly claiming that which is regarded as the present invention, the objects and advantages of this invention may be more readily ascertained from the following description of the preferred embodiments.

The oral composition of the invention comprises a desensitizing salt and sodium bicarbonate. Additional ingredients may also be added as appropriate.

The oral composition may be any suitable delivery vehicle for delivering desensitizing salts to the affected teeth. Acceptable vehicles include, but are not limited to, aqueous solutions, dentifrices, mouthwashes, chewing gums, lozenges and aerosol sprays.

Desensitizing salts include, but are not limited to, known potassium and strontium desensitizing salts, such as strontium chloride, potassium nitrate, potassium chloride, potassium oxalate, potassium citrate, potassium bicarbonate, strontium chloride and strontium acetate. These salts may be present in any particular composition as hydrates of the salt. Other salts that have a desensitizing effect may also be used in the invention.

One known method for delivering desensitizing salts to affected teeth is through the application of an aqueous solution containing the salt directly to the affected tooth. This method is generally employed by dentists in an office procedure. The preferred salts for use in this method are potassium salts, especially potassium nitrate. Strontium salts may also be used, either alone or in combination with potassium salts. The composition preferably comprises from about 0.07% by weight to about 25% by weight of the solution, more preferably about 1% to about 20% by weight of the solution and most preferably about 10% of the solution. In order to successfully mask the unpleasant taste of the salt, sodium bicarbonate should comprise from about 2% by weight to about 40% by weight of the solution. The solution may be applied with a cloth or wipe or with any other suitable applicator.

The solution may also comprise other ingredients useful in treating dental conditions such as sources of fluoride and other agents commonly applied to teeth that do not interfere with the desensitizing action of the salt.

The invention may also be utilized in a desensitizing mouthwash or rinse. Desensitizing mouthwashes and rinses are similar to aqueous solutions except that the may comprise cosolvents, such as ethanol, or other added ingredients.

Mouthwashes and rinses are applied to the affected tooth or teeth differently from aqueous solutions, which are usually coated or painted onto the affected tooth or teeth. In addition, mouthwashes or rinses are usually applied daily to the affected areas. Preferably, therefore, the desensitizing salt comprises from about 0.02% to about 10% by weight of the mouthwash or rinse, and sodium bicarbonate comprises from about 0.5% to about 5% by weight of the mouthwash or rinse.

A dentifrice made in accordance with the invention may be in any acceptable form known in the dentifrice industry, including powders, creams and gels. The dentifrice will typically comprise from about 0.5% to about 25% by weight of the desensitizing salt. In the case of potassium nitrate, the salt preferably comprises from about 0.5% to about 20% of the dentifrice and most preferably about 5% of the dentifrice. In the case of strontium chloride, present in decahydrate form, the dentifrice preferably comprises from about 1% to about 30% strontium chloride, more preferably from about 5% to about 20%, and most preferably about 10% by weight.

In order to mask the taste of the desensitizing salts in the solution fully, sodium bicarbonate should be present from about a 1:1 ratio (on a weight basis) to the desensitizing salt to about a 6:1 ratio, although from about a 6:1 ratio to about an 8:1 ratio may also be effective. Preferably the ratio is from about 1:1 to about 5:1, and most preferably about 3:1.

The desensitizing salt in a chewing gum made in accordance with the invention will preferably comprise from about 0.1% by weight to about 5% by weight of the desensitizing salt, more preferably from about 0.2% by weight to about 3% by weight. Since potassium salts especially are considered to be relatively water soluble, very little of the desensitizing salt is generally entrained in the chewing gum, and most of the salt is available for desensitization.

Preferably, the sodium bicarbonate is intimately associated with the desensitizing salt in the chewing gum, and if the desensitizing salt is encapsulated or protected in any manner, the sodium bicarbonate is also preferably encapsulated or protected along with the desensitizing salt so that the release rates of the desensitizing salt and the sodium bicarbonate are substantially equivalent.

The following examples are intended to demonstrate some advantages of the invention but are not intended to limit the scope or content of the invention.

EXAMPLE 1 (Comparative)

In order to show that potassium nitrate has a deleterious effect on organoleptic qualities of toothpaste, thirty-six panelists rated toothpaste formulations with and without potassium nitrate. The respective formulations were as follows:

| | Weight Percent | |
|---|---|---|
| Ingredient | Formulation w/o $KNO_3$ | Formulation w/$KNO_3$ |
| Sodium MFP | 0.834 | 0.834 |
| Potassium nitrate | — | 5.00 |
| Sodium saccharin | 0.3 | 0.3 |
| Fumed silica | 0.4 | 0.4 |
| Humectant | 24.00 | 24.00 |
| Hydroxyethylcellulose | 1.2 | 1.2 |
| Abrasives | 36.00 | 36.00 |
| Sodium lauryl sulfate | 1.50 | 1.50 |
| Flavor | 1.10 | 1.10 |
| Purified water | q.s. to 100% | q.s. to 100% |

The panelists significantly preferred the product without potassium nitrate for foaming and a directional difference was also indicated for aftertaste. Although no other statistically material differences were observed, the product without potassium nitrate received numerically superior ratings for all attributes examined and overall. This result suggests that the lower performance on foaming and aftertaste due to the presence of potassium nitrate may have had deleterious "spill-over" effects on the other hedonic attributes of the toothpaste formulations. The results are summarized in Table 1.

TABLE 1

Preference Ratings For Dentifrices of Example 1 (n = 36)

| Attribute | No Difference | w/o $KNO_3$ | w/ $KNO_3$ | p |
|---|---|---|---|---|
| Appearance | 1 | 22 | 13 | 0.18 |
| Taste | 0 | 20 | 16 | 0.62 |
| Consistency | 0 | 21 | 15 | 0.41 |
| Foaming | 0 | 25 | 11 | 0.03 |
| Aftertaste | 0 | 23 | 13 | 0.13 |
| Overall | 0 | 22 | 14 | 0.24 |

EXAMPLE 2

Thirty panelists compared a toothpaste formulation containing potassium nitrate and baking soda with several commercial toothpastes containing baking soda but not containing potassium nitrate: Arm & Hammer® toothpaste with baking soda; Colgate® toothpaste with baking soda; and Crest® toothpaste with baking soda. The mean scores and standard deviation (SD) are shown in Table 2. The scale is from 1 to 9, where 1 is a low score and 9 is a high score, except for Flavor Intensity, where 1 is too weak and 9 is too strong, Consistency, where 1 is too thin and 9 is too thick, and Foaming where 1 is not enough foam and 9 is too much foam.

The tested toothpaste formulation was as follows:

| Ingredient | % by Weight |
|---|---|
| Potassium nitrate | 5.0 |
| Sodium saccharin | 0.35 |
| Sodium fluoride | 0.243 |
| Sodium bicarbonate | 25.0 |
| Hydrated silica | 10.0 |
| Titanium oxide | 0.5 |
| Fumed silica | 1.0 |
| Humectant | 24.0 |
| Hydroxyethylcellulose | 1.2 |
| Sodium lauryl sulfate | 1.5 |
| Flavor | 1.3 |
| Methyl paraben | 0.05 |
| Pr - paraben | 0.05 |
| Purified water | q.s. to 100.00 |

TABLE 2

Preference Ratings For Dentifrices of Example 2 (n = 30)

| Attribute | Example Mean (SD) | Arm & Hammer Mean (SD) | Colgate Mean (SD) | Crest Mean (SD) | p-value |
|---|---|---|---|---|---|
| Appearance | 6.1 (1.0) | 4.1 (1.6) | 5.6 (1.7) | 5.2 (1.7) | 0.0001 |
| Taste | 5.1 (1.9) | 4.7 (1.8) | 5.6 (2.0) | 5.6 (1.8) | 0.16 |
| Flavor Intensity | 5.0 (1.5) | 5.2 (1.3) | 4.8 (1.4) | 5.6 (1.2) | 0.11 |
| Consistency | 4.1 (1.3) | 3.9 (1.8) | 4.3 (1.5) | 4.2 (1.4) | 0.79 |
| Foaming | 3.7 (1.3) | 3.3 (1.4) | 3.8 (1.5) | 3.4 (1.2) | 0.17 |
| Aftertaste | 5.4 (1.9) | 5.2 (2.1) | 5.7 (1.8) | 5.5 (2.0) | 0.75 |
| Overall | 5.0 (1.7) | 4.1 (1.9) | 5.4 (2.1) | 5.0 (2.1) | 0.03 |

These results confirm that the presence of potassium nitrate, which ordinarily has a negative effect on the hedonic and organoleptic properties of a toothpaste, surprisingly, is completely masked by sodium bicarbonate, and the organoleptic and hedonic qualities of a toothpaste containing potassium nitrate and sodium bicarbonate are surprisingly equivalent to general commercial baking soda toothpastes.

EXAMPLE 3

Another sensory study was conducted to determine the optimum concentration of sodium bicarbonate in toothpaste to achieve effective masking of the taste of the potassium salt. A series of toothpastes containing 5% potassium nitrate and varying concentrations of sodium bicarbonate were formulated and subjected to sensory evaluation. Product attributes such as mintiness, sweetness, saltiness, bitterness and metallic taste were rated on a scale of 0–100 by a series of users of dentifrices in blank metal tubes. The results are set out in Table 3.

TABLE 3

Mean and Standard Deviation for Attribute Intensity of Dentifrices of Example 3

| Attribute | 0%<br>n = 33 | 3%<br>n = 34 | 8%<br>n = 33 | 15%<br>n = 33 | 25%<br>n = 32 | 30%<br>n = 33 |
|---|---|---|---|---|---|---|
| Mintiness | | | | | | |
| Mean | 48.0 | 47.0 | 49.6 | 55.7 | 44.9 | 56.4 |
| Std | 28.7 | 31.6 | 28.1 | 25.4 | 26.7 | 24.4 |
| p-value | 0.19 | | | | | |
| Sweetness | | | | | | |
| Mean | 32.2 | 30.2 | 33.5 | 42.5 | 39.2 | 32.4 |
| Std | 25.4 | 25.8 | 23.6 | 25.2 | 28.9 | 23.1 |
| p-value | 0.14 | | | | | |
| Saltiness | | | | | | |
| Mean | 23.0 | 15.3 | 15.6 | 16.0 | 32.0 | 28.9 |
| Std | 29.1 | 23.0 | 17.1 | 22.6 | 33.1 | 28.5 |
| p-value | 0.002 | | | | | |
| Bitterness | | | | | | |
| Mean | 31.3 | 28.5 | 26.3 | 12.5 | 17.5 | 24.3 |
| Std | 28.5 | 31.8 | 29.8 | 14.8 | 19.7 | 23.8 |
| p-value | 0.002 | | | | | |
| Metallic | | | | | | |
| Mean | 18.0 | 15.1 | 10.6 | 10.4 | 12.9 | 13.4 |
| Std | 23.5 | 23.4 | 12.7 | 15.7 | 15.8 | 16.0 |
| p-value | 0.25 | | | | | |

The results set forth in Table 3, as shown graphically in the attached figures, show the effect of baking soda on dentifrices containing potassium nitrate as a desensitizer.

Perceived mintiness appears to go up significantly from about a 1:1 ratio of baking soda to potassium nitrate to a ratio of about 3.5:1. The mintiness then appears to increase again beginning at about a 5.2:1 weight ratio.

Sweetness is apparently increased from about a 1:1 weight ratio to about a 6:1 weight ratio of baking soda to potassium nitrate. The sweetness increase is pronounced from about a 2:1 weight ration to about a 5:1 weight ratio, and the peak is at about a 3:1 weight ratio of baking soda to potassium nitrate.

Thus it appears that baking soda enhances to positive flavor attributes of the dentifrice in a weight ratio from about 1:1 to about 6:1, preferably from about 1:1 to about 5:1, and most preferably about 3:1, as stated above.

The negative flavor attributes of a 5% potassium nitrate dentifrice are also reduced by the addition of baking soda. Saltiness is reduced apparently immediately upon introduction of baking soda to a weight ratio of about 4:1 baking soda to potassium nitrate. The effect is apparently strongest from a ratio of about 0.6:1 to about 3:1. Bitterness is also reduced apparently immediately upon introduction of baking soda to a weight ratio in excess of 6:1. The reduction is pronounced at a ratio of about 2:1 to about 4:1, and is most pronounced at a ratio of about 3:1.

Metallic taste also reduced apparently immediately upon introduction of baking soda to a weight ratio in excess of 6:1. The effect is pronounced from about 1:1 to about 5:1, and is most pronounced from about 2:1 to about 3:1.

EXAMPLES 4–5

Mouthrinses in accordance with the invention were prepared by combining the following ingredients in an aqueous environment:

| Ingredient | Wt. %<br>Example 4 | Wt. %<br>Example 5 |
|---|---|---|
| Potassium nitrate | 2.5 | — |
| Potassium chloride | — | 2.0 |
| Sodium saccharin | 0.10 | 0.15 |
| Sodium benzoate | 0.10 | 0.10 |
| Sodium bicarbonate | 2.5 | 2.0 |
| Poloxamer 407 | 2.0 | — |
| Polysorbate 60 | — | 2.5 |
| Ethyl Alcohol | 4.0 | 5.0 |
| Flavor | 0.15 | — |
| FD&C Blue #1 | 0.0005 | — |
| FD&C Yellow #10 | 0.0005 | — |
| FD&C Red #28 | — | 0.001 |
| Purified water | q.s. to 100 | q.s. to 100 |

EXAMPLES 6–7

Dentifrice compositions in accordance with the invention were prepared by combining the following ingredients:

| Ingredient | Wt. %<br>Example 6 | Wt. %<br>Example 7 |
|---|---|---|
| Potassium nitrate | 5.0 | — |
| Potassium chloride | — | 3.8 |
| Sodium saccharin | 0.3 | 0.3 |
| Sodium fluoride | 0.243 | 0.243 |
| Sodium bicarbonate | 20.0 | 20.0 |
| Hydrated silica | 15.0 | 16.0 |
| Titanium oxide | 1.0 | 1.0 |
| Fumed silica | 1.0 | 1.0 |
| Humectant | 20.0 | 22.0 |
| CMC 12M31xP | 1.6 | 1.6 |
| Sodium laurel sulfate | 1.5 | 1.5 |
| Flavor mix | 1.3 | 1.3 |
| Methyl paraben | 0.05 | 0.05 |
| Propyl paraben | 0.05 | 0.05 |
| Purified water | q.s. to 100 | q.s. to 100 |

EXAMPLES 8–10

Chewing gums in accordance with the invention were prepared by combining the following ingredients:

| Ingredient | Wt. %<br>Ex. 8 | Wt. %<br>Ex. 9 | Wt. %<br>Ex. 10 |
|---|---|---|---|
| Chewing gum base (Dreyfus) | 25.0 | 30.0 | 35.0 |
| Hydrogenated glucose syrup | 11.0 | 13.0 | 15.0 |
| Water | 0.9 | — | 0.5 |
| Flavor | 0.4 | 0.4 | 0.5 |
| Glycerin | 1.0 | 1.5 | 2.0 |
| Lecithin | 0.4 | 0.4 | 0.4 |
| Calcium saccharin | 0.1 | 0.1 | 0.1 |
| Sorbitol powder | q.s. to 100 | q.s. to 100 | q.s. to 100 |
| Xylitol | — | 5.0 | — |
| Sodium carbopol | — | — | 1.0 |
| Plasticizer | 0.1 | 0.2 | — |
| Sodium fluoride | 4ppm | — | — |
| Sodium monofluorophosphate | — | 0.03 | — |
| Sodium bicarbonate | 1.6 | 3.0 | 6.0 |

-continued

| Ingredient | Wt. % Ex. 8 | Wt. % Ex. 9 | Wt. % Ex. 10 |
|---|---|---|---|
| Potassium nitrate | 1.0 | — | — |
| Potassium chloride | — | 0.8 | — |
| Potassium citrate | — | — | 2.0 |

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. A formulation for treating dental hypersensitivity comprising:
   (a) an effective desensitizing amount of a desensitizing salt; and
   (b) sodium bicarbonate in an effective taste masking amount,
   wherein the weight ratio of (a) to (b) is about 1:1 to 1:8 and wherein said desensitizing salt is potassium nitrate and wherein said formulation is selected from the group consisting of aqueous solution, mouthwash and dentrifice.

2. The formulation of claim 1, wherein said formulation is an aqueous solution.

3. The formulation of claim 2, wherein said desensitizing salt comprises from about 0.07% by weight to about 25% by weight of said solution.

4. The formulation of claim 3, wherein said desensitizing salt comprises from about 1% to about 20% by weight of said solution.

5. The formulation of claim 4 wherein said desensitizing salt comprises about 10% of said solution.

6. The formulation of claim 5, wherein said ratio is from about 1:1 to about 5:1.

7. The formulation of claim 5, wherein said ratio is about 3:1.

8. The formulation of claim 1, wherein said formulation is a mouthwash.

9. The formulation of claim 8, wherein said desensitizing salt comprises up to about 10% by weight of said mouthwash.

10. The formulation of claim 9, wherein said desensitizing salt comprises from about 0.2% to about 5% by weight of said mouthwash.

11. The formulation of claim 10, wherein said ratio is from about 1:1 to about 5:1.

12. The formulation of claim 11, wherein said ratio is about 3:1.

13. The formulation of claim 1, wherein said formulation is a dentifrice.

14. The formulation of claim 13, wherein said desensitizing salt comprises from about 0.5% to about 20% by weight of said dentifrice.

15. The formulation of claim 13, wherein said desensitizing salt comprises about 5% of said dentifrice.

16. The formulation of claim 15, wherein said ratio is from about 1:1 to about 5:1.

17. The formulation of claim 16, wherein said ratio is about 3:1.

18. A method for treating hypersensitive teeth comprising the step of applying the formulation of claim 1 to a hypersensitive tooth for a time sufficient to aid in desensitization of said tooth.

* * * * *